(12) United States Patent
Soble et al.

(10) Patent No.: US 8,046,226 B2
(45) Date of Patent: Oct. 25, 2011

(54) SYSTEM AND METHODS FOR REPORTING

(75) Inventors: Jeffrey Soble, Highland Park, IL (US); James Roberge, Darien, IL (US)

(73) Assignee: Cyberpulse, L.L.C., Highland Park, IL (US)

( * ) Notice: Subject to any disclaimer, the term of this patent is extended or adjusted under 35 U.S.C. 154(b) by 951 days.

(21) Appl. No.: 12/009,605

(22) Filed: Jan. 18, 2008

(65) Prior Publication Data
US 2009/0187407 A1 Jul. 23, 2009

(51) Int. Cl.
*G10L 11/00* (2006.01)
*G06F 17/27* (2006.01)
*G06F 17/20* (2006.01)

(52) U.S. Cl. .............................. 704/270; 704/9; 715/255
(58) Field of Classification Search ........................ None
See application file for complete search history.

(56) References Cited

U.S. PATENT DOCUMENTS

| | | | |
|---|---|---|---|
| 5,051,924 A * | 9/1991 | Bergeron et al. ............. 704/200 |
| 5,168,548 A * | 12/1992 | Kaufman et al. ............. 704/200 |
| 5,255,187 A | 10/1993 | Sorensen |
| 5,465,378 A * | 11/1995 | Duensing et al. ............. 715/233 |
| 5,765,130 A * | 6/1998 | Nguyen ........................ 704/233 |
| 6,024,699 A | 2/2000 | Surwit et al. |
| 6,063,026 A | 5/2000 | Schauss et al. |
| 6,076,060 A | 6/2000 | Lin et al. |
| 6,113,540 A | 9/2000 | Iliff |
| 6,154,750 A | 11/2000 | Roberge et al. |
| 6,192,112 B1 | 2/2001 | Rapaport et al. |
| 6,216,104 B1 * | 4/2001 | Moshfeghi et al. ........... 704/260 |
| 6,270,456 B1 | 8/2001 | Iliff |
| 6,304,848 B1 | 10/2001 | Singer |
| 6,381,611 B1 | 4/2002 | Roberge et al. |
| 6,401,085 B1 | 6/2002 | Gershman et al. |
| 6,440,066 B1 | 8/2002 | Bardy |
| 6,514,201 B1 * | 2/2003 | Greenberg .................... 600/437 |
| 6,601,026 B2 | 6/2003 | Appelt et al. |
| 6,589,169 B1 | 7/2003 | Surwit et al. |
| 6,684,276 B2 | 1/2004 | Walker et al. |
| 6,801,916 B2 | 10/2004 | Roberge et al. |
| 6,849,045 B2 | 2/2005 | Iliff |
| 7,043,426 B2 | 5/2006 | Roberge et al. |
| 7,082,440 B2 | 7/2006 | Ogino et al. |
| 7,155,447 B2 | 12/2006 | Roberge et al. |
| 7,321,861 B1 * | 1/2008 | Oon ................................. 705/3 |
| 7,496,500 B2 * | 2/2009 | Reed et al. ........................ 704/9 |
| 2002/0082825 A1 * | 6/2002 | Rowlandson et al. ............ 704/9 |
| 2004/0122790 A1 | 6/2004 | Walker et al. |
| 2004/0172245 A1 * | 9/2004 | Rosen et al. .................. 704/235 |
| 2005/0055215 A1 * | 3/2005 | Klotz ............................ 704/275 |
| 2007/0118399 A1 | 5/2007 | Avinash et al. |
| 2007/0198250 A1 * | 8/2007 | Mardini ............................ 704/9 |

* cited by examiner

*Primary Examiner* — Brian Albertalli
(74) *Attorney, Agent, or Firm* — Valauskas Corder LLC

(57) ABSTRACT

The present invention relates to a system and methods for preparing reports, such as medical reports. The system and methods advantageously can verbalize information, using speech synthesis (text-to-speech), to support a dialogue between a user and the reporting system during the course of the preparation of the report in order that the user can avoid inefficient visual distractions.

47 Claims, 8 Drawing Sheets a) The coronary circulation is right dominant. The ___ coronary arteries are patent without significant disease. The left anterior descending artery has a ___ stenosis in the ___ segment.

b) The coronary circulation is right dominant. The left main, left circumflex, and right coronary arteries are patent without significant disease. The left anterior descending artery has a 75% stenosis in the mid segment.

c) The coronary circulation is right dominant *with no bypass grafts*. The left main, left circumflex, and right coronary arteries are patent without significant disease. The left anterior descending artery has a 75% stenosis in the mid segment. *Recommend stenting of this lesion.*

FIG. 1

St. Elgius Hospital Radiology Services

Name: John Smith  Attending physician: Dr. Jane Doe
MR#: 123456789  Referring physician: Dr. William Jones
DOB: 01/01/1950

Chest CT report
12/10/2007

Clinical history
*Indications for study. Pertinent patient diagnoses and symptoms*

Procedure
*Description of procedure performed, including doses of administered radiation, contrast agents, and medications*

Findings
*Observations from study grouped into sections based on anatomy (e.g., lungs, liver, etc.), pathology (e.g., mass, lesion, etc.), or subprocedure*

Comparisons
*Comparison of findings in current study with those in a prior study*

Impressions
*Diagnoses -- including differential diagnoses. Recommendations for follow-up or additional studies*

FIG. 4

SYSTEM AND METHODS FOR REPORTING

FIELD OF THE INVENTION

The present invention relates to a system and methods for reporting, such as medical reporting. More particularly, the present invention is directed to a system and methods by which a reporting system verbalizes information through speech synthesis (text-to-speech) conversion.

The reporting system of the present invention is useful in a variety of industries including medical, sales, financial, legal, tax, insurance, aviation and research and for a variety of purposes including the generation of reports.

BACKGROUND OF THE INVENTION

In many industries, reports are used to present, explain, or put into context various types of information including data, results of tests, information regarding procedures available or preferred, and the status of the project that may be the subject of the report. A report may include content in a variety of forms including static or dynamic images, text, and transcripts of verbal communications. For purposes of this application, this organized collection of content is termed a "report".

In the medical industry, reports pertaining to the treatment and care of a patient are regularly generated. For purposes of this application, the term "medical report" refers to any documentation related to the treatment and care of a patient including, but not limited to test reports, procedural reports, surgical notes, or clinical notes. Medical reports may include a variety of forms of content, such as that described above. For example, the content may be text or static or dynamic images providing information regarding the patient's medical condition, such as the patient's history, symptoms, and diagnoses. The report content may also include information regarding medical procedures, including the details of the procedures to which the patient was subjected or offered, or the results of the procedures and the complications, if any, which the patient experienced. The content of a medical report may include also data directed to a current procedure which a patient is undergoing including measurements and lab reports. Additionally, the content within a medical report may include the observations, interpretations and recommendations of a treating physician, a consulting physician, or other caregiver. Medical reports are typically organized into sections, such as according to anatomy, pathology, and/or the content or subjects mentioned above. Medical reports may include additional information regarding the patient's insurance, family members, and orders and directions relevant to the patient's care.

Medical reports are usually created by a medical professional such as a doctor or nurse or other caregiver or agent such as a technician. Those that prepare a medical report are termed "medical professional" in this application. The medical professional preparing such a report often reviews results collected, information gathered, and other content on or relevant to a patient prior to creating the report—including lab reports, prior medical reports, and pre-study paperwork such as orders, patient-supplied datasheets, clinical notes, and electronic medical records ("EMRs"), as well as information from and notes taken of conversations directly with the patient or one or more of his or her family members.

Medical reports are prepared by one or more of a variety of methods, including handwriting, typing, dictation, speech recognition, and structured reporting. Dictation allows a medical professional to speak the substance of a report into a recording device. From this recording, a transcript is later prepared, often manually. The medical professional typically must review the transcribed report for accuracy. After the professional is satisfied with the accuracy of the transcript, a final report is prepared.

There are a variety of disadvantages associated with the traditional approaches to preparing a report. For example, with respect to transcriptions, because typically someone other than the author of the report actually prepares the transcript from the recording made by the professional, errors result from the transcriber's inability to accurately identify what the professional said. Spelling and grammatical errors often also appear in the transcript. In addition, it takes time for a dictated report to be transcribed, reviewed, edited, and approved for final distribution. This delay is undesirable and can further impact not only immediate patient care—particularly when the patient is in a critical condition—but also long term healthcare costs.

Speech recognition technologies are known. These technologies permit a user, such as a medical professional, to speak into a recording device and, through the use of speech recognition software, a transcription for the medical report can be prepared. For purposes of this application, speech recognition is defined to be synonymous with voice recognition. The transcription or report that results from this process can then be revised by the professional, either on a display device (real-time or off-line) or on paper (off-line), and edited, if necessary. This approach, however, is not problem-free.

Problems with conventional speech recognition technologies include erroneous transcription. Transcription error rates typically range from 5% to 15% depending on the speaker's skill with the language used to prepare the report, the environment, and vocabulary. Equally important, speech recognition errors are unpredictable, with even simple words and phrases being misrecognized as completely nonsensical words and phrases. In order to prevent these recognition errors from appearing in the final report, the medical professional must very carefully review the transcribed report. Given the large number of reports that many medical professionals are required to prepare in a single day, they often attempt to review the transcribed text as it is produced by speech recognition software by glancing at the transcribed text on the display device while receiving or analyzing the data or image about which the transcription or report is being prepared. In some reporting environments, however, this approach is time consuming and can cause errors in the transcribed text to be overlooked and/or cause errors to creep into the report. For radiologists, the traditional approach to report preparation using speech recognition software is particularly problematic. It is not easy for a radiologist to go from examining the intricate details of an X-ray to reviewing written words, then returning to examining the X-ray. The radiologist invariably loses the exact spot on the X-ray he or she was examining before reviewing the text transcribed from his or her dictated observations. In addition, the displayed report occupies space on the display device, preventing it from illustrating other content, such as images.

Structured reporting technologies are known also. They permit, for example, a medical professional to record information using a computer user interface, such as a mouse and/or keyboard. The medical report is automatically generated from this information in real-time. Structured reporting may also include the use of speech recognition software to support navigation, data entry, and editing such as adding text or images to the medical report.

The primary problem with structured reporting technologies is that it may take a medical professional what they may view as an unacceptable amount of time to complete a structured report using a traditional computer user interface. Medical reports often require very large structured reporting data sets. As a result, navigating these data sets may be complex and entering findings may become a lengthy process that requires time that medical professionals could use more effectively attending to other tasks, such as seeing additional patients, preparing additional medical reports, or reading medical literature.

Attempts have been made to improve the efficiency with which reports, including medical reports are prepared. Often these methods use what are termed "macros". A "simple macro" is a text string identified by a name. For example, a macro corresponding to the text string "No focal liver mass or intrahepatic duct dilatation" may be identified by the macro name "Normal liver". "Macro templates" are macros that include a mix of text strings and placeholders, such as blank slots or pick-lists. The placeholders indicate where the user may—or must—insert additional text. Some technologies that record and transcribe the spoken word utilize macros. For example, by mentioning the name of the macro in a voice command or a user interface, the associated text and placeholders are positioned in the medical report. The text can be edited and any placeholders filled in by the medical professional to generate narrative text.

Certain simple macros and the names by which each is identified are shown in the following chart. Each string of text (right column of chart) can be orally identified to the system that is being used to prepare the report by simply mentioning the name of the macro (left column of chart).

| Macro Name | Text String |
| --- | --- |
| "Right dominant" | The coronary circulation is right dominant. |
| "Normal coronaries" | The _____ coronary arteries are patent without significant disease. |
| "LAD lesion" | The left anterior descending artery has a _____ stenosis in the _____ segment. |

FIG. 1 illustrates how a portion of a CT angiography report can be prepared from these macros. More specifically, portion a) of FIG. 1 illustrates how the three macros above can be organized to form a portion of the entire report directed to the condition of a certain patient. Portion b) of FIG. 1 illustrates how the medical professional may fill in the placeholders in the text. Portion c) of FIG. 1 shows that an edit can be made to the first macro statement. The edit is shown in italics. An addition of a new statement is shown as a fourth sentence (also in italics).

Some systems allow reports to be generated through the use of an extensive set of macros or macro library. A macro library may include tens, hundreds, or even thousands of macros created, for example, by individual users to match a specific reporting style, or by commercial vendors and licensed as "comprehensive" macro sets. While large macro sets can be advantageous and permit a wide variety of reports to be prepared more rapidly under a wider range of circumstances, the sheer size of the library can be a disadvantage. Memorizing all of the macro names may be simply infeasible for the user. To lessen this problem, large macro libraries may include a user interface that categorizes macros and provides for visual navigation of the extensive macro library. However, this navigation approach has all of the disadvantages of a structured reporting user interface. Navigating an on-screen interface that categorizes the macros in the macro library takes significant time. It also requires a medical professional to remove his or her visual focus from other clinical activities, such as reviewing the medical images which are the subject of the report or even attending to a patient. Navigating an on-screen interface may be a significant distraction that may lead to errors, as well as increase the time it takes to prepare a report.

In addition, macros alone are usually insufficient to complete a medical report. Many medical reports consist of a combination of text strings recorded as macros (and perhaps subsequently edited) and unstructured free-form statements entered directly by the user (transcribed or typed).

Overall, dictation, speech recognition, and structured reporting (including structured reporting using traditional macros) constrain medical reporting, for example, with respect to speed and visual focus. Medical professionals need to create reports quickly and efficiently, and transmit the resulting reports rapidly to other medical professionals (e.g., referring physicians). Again, with respect to radiology, a single user may need to produce many, perhaps over a hundred reports in a single day. Preparing the report requires intense visual focus on one or more images, such as X-ray images, computed tomography ("CT") scans, and ultrasound loops. Having to look away from an image to a computer user interface on which the text appears, is a significant time consuming distraction that again can lead to errors and longer reporting times.

As a result, there is a need for a reporting system that allows users, such as medical professionals, to create a report in an efficient manner while maintaining their visual focus on that subject about which the report is being written or on a subject or object different from that about which is the report is being prepared. More specifically, there is a need for a system that permits a user to receive information from a report aurally, thereby not requiring the user to distract his or her visual focus.

SUMMARY OF THE INVENTION

The present invention is discussed in the following largely with reference to the medical industry, but the present invention is applicable to a variety of contexts and environments, each of which may utilize or benefit from the utilization of a reporting system to create documentation, for example, for sales, financial, legal, tax, insurance, aviation and research purposes.

The present invention is a system and methods by which a report may be prepared during the course of an activity, such as performing a job function. In the medical industry, for example, a surgical note may be documented in a report during surgery, a gastroenterological report could be prepared during a colonoscopy procedure, or a pathology analysis may be documented during analysis of a sample. In non-medical environments, for example, a building inspection report may be prepared as an inspector conducts a building walkthrough, an incident report may be written as a police officer investigates an accident scene, a flight log may be created as a pilot is flying an aircraft, or a business development report may be created as an analyst reviews accounting data and supporting documents.

The present invention also allows a user to create a report in situations in which the user finds it difficult or distracting to interact with a keyboard, mouse, or display such as an air safety inspector crawling through an aircraft, a nurse completing a clinical note while walking to the next patient's room, or a construction foreman preparing a daily status report while moving through a busy construction site.

The present invention provides an enhanced system and methods for reporting, such as medical reporting. The enhanced system and methods for reporting "verbalizes" information, that is, reads information aloud such that it is audible to the user through speech synthesis—where speech synthesis is the artificial production of human speech. It is contemplated the present invention may verbalize information in real-time as well as off-line. Hearing the information—rather than reading it on-screen—eliminates the problems discussed herein, including errors and distraction, while also freeing up the display on which a medical report is typically illustrated. By permitting a user to receive information aurally, the user is free to use his or her eyes to receive and analyze other information, and overall use his or her time more efficiently.

Generally, the reporting system according to the present invention receives information as user input via a user input device. The system processes the information and performs a task, such as executing the instruction which the user provided. The system then prepares an appropriate response, and communicates it to the user as voice output on a voice output device. The user can repeat this process of submitting information to the system via a user input device, having the system process the information and perform tasks according to the instruction given by the user, then communicating an appropriate response to the user as needed and until the report is completed.

More specifically, the reporting system according to the present invention permits a user to create a report by submitting information to the system in the form of one or more user inputs through the use of a user input device. For purposes of this application, a user input device may be a keyboard, mouse, touch screen, keypad, microphone, dictation device, or speech recognition mechanism, to name a few. In embodiments of the system that use speech recognition, the user input can also be in the form of a spoken word or words. Other forms of user input can be information submitted via keyboard entry, mouse clicks or drag-and-drop, touch screen selections, and button presses.

After receiving the information as user input via the input device, the system processes the information according to the instructions received from the user. Processing the information may include executing a heuristic algorithm to perform a task, or accessing a database to correlate the information received from the user to the task that the system is being directed to perform.

The tasks that the system performs result from processing the information. For example, the tasks may include: specifying a report format such as CT report, cardiology report, radiology report; entering a narrative statement into the report; recording information; choosing a section in the report; picking a statement in the report; carrying forward report content from a prior report into the current report; annotating or commenting upon a portion of the report content such as an image; reviewing or examining the current report or prior report; selecting a macro from a macro library; hierarchical navigation of a macro library; heuristic selection from the macro library; navigation within the report; matching the information to a section or statement of the report or the name or contents of a macro verifying the report content with respect to standards regarding report completeness; issuing warnings or alerts based on the presence or absence of specific information in the report content; and, retrieving and reviewing data such as patient data, and literature such as medical literature.

In line with the task that the system is being directed to perform, the system determines an appropriate response. For purposes of this application, "response" is that conveyed from the system to the user. Responses can vary and result from the task performed. Responses include, for example, acknowledgement of the user input, such as that information was received, a command was invoked, or a macro was triggered; results of report content changes, including additions, deletions, and edits; verification, including report content recorded by a user, report content recorded using a macro, or the names of the macros that the user used while preparing the report; system prompts listing choices requiring a refined selection by the user, such as a list of macros that match the user input; system prompts for additional information that is needed to complete a report, such as strings of text required to complete the options in a macro template; warnings; comments regarding the report, including portions of the report as well as images; alerts from conflicts, such as problems with the user input or incompatibility of the information with either the current report or a previous report; and narrative, such as user requested information including patient data, literature such as medical literature, and report content.

More specifically, the report content in the response may include the entire report, or a portion or portions thereof, such as: text, information in a static or dynamic image of the patient, as well as content related to the patient's medical condition including history, symptoms, and diagnoses; information regarding medical procedures to which the patient was subjected or offered, including descriptive details regarding procedures, results, and complications; information regarding medical results including observations, interpretations and recommendations; medical data including measurements, lab reports, and historic information regarding a patient, such as medical history. In addition, the report can be presented as an abbreviated report summary containing, for example, the names of the macros used in creating the report and the contents of any statements that were edited or added by the user. This report summary allows a user to rapidly review a report by focusing on the specifics of what the user said rather than on what was recorded by familiar macros. The resultant medical reports can be organized into sections, based on anatomy, pathology, and the content mentioned above and may include additional information regarding the availability of insurance for the patient's care, description of the patient's family members, and include orders and directions. Again, the response of the system may include any or all report content, which is further verbalized as voice output.

Either during the preparation of the report or when the report is complete, the system advantageously permits a user to listen to the system responses as voice output on a voice output device, such as a speaker or headset. In one embodiment, voice output is synthesized speech. Other types of voice output are contemplated such as non-synthetic speech. The synthesized speech is generated by forming a phonetic representation of the system response. Phonetic representations may be formed by using a dictionary of tuples that pair words with the corresponding phonemes; by forming phonetic representations of words based on the phonetic characteristics of the characters in a word; or a combination thereof. The resulting phonetic representation is then processed using a model of human voice characteristics, such as the vocal tract, to create a completely synthetic voice output of the system response. This synthesis may be performed by dedicated speech synthesis hardware or by speech synthesis software in conjunction with standard sound generation hardware such as a computer sound card.

The act of the user listening to the voice output, or synthesized speech, for purposes of this application is termed herein as "review". It is contemplated that the voice output of the system response is not limited to a fixed set of speech and therefore is not limited to pre-recorded or pre-converted responses.

In one embodiment, the present invention is a reporting system that utilizes speech recognition. An object of the present invention is to use speech synthesis and speech recognition so that an unprompted conversational dialogue between the system and the user can occur. For example, the user can speak a word or words which are processed by a speech recognition mechanism and the reporting system, through the use of speech synthesis, can respond aurally, where "speech recognition mechanism" refers to speech recognition software, an audio input device and optionally an audio output device. In one embodiment, the speech recognition mechanism is a microphone and speaker connected to a computer or other electronic device capable of executing speech recognition software such as a speech recognition algorithm. It is contemplated that the audio input device and audio output device can be integrated such as in a wireless headset. Both the user and the reporting system can speak unprompted—even permitting interruptions during the dialogue such as mid-sentence or mid-speech.

In embodiments of the present invention wherein the reporting system utilizes speech synthesis and speech recognition, user input from the user may be in the form of an utterance such as unstructured statements, otherwise referred to herein as "free-form statements", structured statements, otherwise referred to herein as "fixed-form statements", and a combination thereof referred to herein as "mixed-form statements". Free-form statements include, for example, narrative speech such as comments, observations, and interpretations to name a few. Fixed-form statements include pre-defined speech such as commands and user acknowledgements. An example of a mixed-form statement includes a command (fixed-form) with one or more parameters (free-form).

It is contemplated that, in one embodiment of the system according to the present invention, the system directs and guides the user through the creation of the report. In another embodiment of the system according to the present invention, the user directs and guides the system through the creation of the report. Thus, the information that a user enters into the system and the responses that the system communicates may be the same, such as prompts, acknowledgements, and commands. For purposes of this application, the information that a user enters in the system will be denoted with the use of the term "user", e.g., user prompt, and the responses that the system communicates will be denoted with the term "system", e.g., system prompt.

One embodiment of the present invention also contemplates a reporting system that uses speech synthesis and speech recognition to support a prompted conversational dialogue in which user and system take turns while interacting. For example, a system-directed prompted conversational dialogue allows creation of the report through a series of reporting system prompts that guide the user to enter information. An example of a user-directed conversational dialogue is where the user issues commands, which direct the reporting system in the creation of the report.

Voice output of a report may be activated manually, verbally by the user, or automatically such as by speech recognition software. Review can occur either during the reporting process or when the report is complete.

In embodiments where voice output is activated manually, users may likely invoke the voice output periodically or when he or she feels that circumstances such as ambient noise, interruptions, or difficult words may have negatively impacted the accuracy of the information, or when the user wishes to confirm the report contents recorded by a macro. For example, to invoke voice output of statements in a section (or portion) of a report, a user may manually enter information via a keyboard or speak information into a speech recognition mechanism, such as the command "Read section Lungs" to activate speech synthesis to read aloud the statements in the "Lungs" section of a medical report.

In embodiments where voice output is activated automatically, speech recognition software may determine when the probability that the input speech has been recognized correctly falls below a specified threshold. Once the probability falls below the threshold, speech synthesis is activated and the recognized text is spoken back to the user. For example, suppose that a user speaks the statement "Abnormal lung function" which the speech recognition software recognizes as "Abnormal lung junction". If the word "junction" was assigned a probability of being correct that is below the specified threshold, the system can automatically invoke speech synthesis to read aloud the statement "Abnormal lung junction" along with a prompt that asks the user to either confirm the statement's accuracy or correct any misrecognitions.

Additionally, the speech synthesized voice output can be saved as an audio file to be listened to later. The audio file can be saved within the report itself, such as part of the narrative or images, or can be saved in a different location such as on an MP3 player.

An embodiment of the present invention permits a user to conduct a speech synthesized review of a report parallel to, or simultaneous with other activities. For example, a medical professional can select and load an X-ray image on a display device for assessment, while simultaneously listening to voice output presenting report contents or other system responses such as patient history, related medical literature, and so forth, without using space on the system display to present this information.

As mentioned above, the present invention allows a user to review literature, such as abstracts, on-line textbooks, or Internet resources related to a particular study, such as a medical study. For example, a medical professional specifies information to a user input regarding what resources or keywords to search such as speaking into a speech recognition user input device the mixed-form statement "Search textbooks 'CT Left ventricular function'" or "Search recent abstracts 'CT Left ventricular function'". The system response is voice output of the resulting material. Again, this can be done while the user is assessing or focusing on other information, such as images.

The present invention allows a user to listen to a synthesized speech response that includes all or a portion of a previously created report, or prior report. Further, while the user is listening or reviewing the prior report, the user can select portions of the prior report for insertion into a new report, or current report. For example, it is quite common for a patient to undergo repetitions of the same type of study or examination over a period of days, months, or years in an effort to determine whether the patient's condition has changed over the chosen period of time. Rather than recording an entirely new report for each study, the present invention allows a user to insert content from a prior report into a new report as appropriate. This may be accomplished by entering information using a speech recognition user input device, such as spoken words, to select the report content. It is contemplated that the user can select report content while it is being read aloud for insertion into the new report.

As another example, an embodiment of the present invention allows a user to select a portion of a report, such as an image or section, and enter information regarding the selected portion which can then be verbalized as voice output. For example, a medical professional might select a region of interest ("ROI") on an X-ray image by clicking the region or by speaking free-from statements regarding the same. The medical professional can enter information such as comments, observations, or interpretations, using a speech recognition user input device. The comments, observations, or interpretations may remain associated with the selected portion of the image or section to be listened to as voice output at a later date when the image or document is reviewed or when the added information alone is reviewed Yet another embodiment of the present invention allows voice output to communicate alerts to a user. For example, the system can verbalize that a portion of a report is potentially incorrect or that the report requires that special procedures be followed such as personally contacting a patient or referring physician regarding the medical report. It is contemplated that the recipient of the alert may be the user preparing the report or may be another user, for example, another medical professional involved in caring for the patient. It is further contemplated that the alert may be transmitted by any technology such as telephone, voice mail, message bank, physician notification system, and Web page.

In another embodiment of the present invention, voice output is used to verbalize responses from a report prepared at least in part using macros. Voice output can be synthesized speech of the macro name, macro content, the text generated by the macro, or a portion of the text generated by the macro. The present invention contemplates speech synthesized voice output of the macro name, macro content, the text associated with a macro either retrospectively—after the macro has been recorded—or prospectively—prior to recording the macro. For example, the user can speak the information "Read macro X" or "Read last macro" using a speech recognition user input device.

In yet another embodiment of the present invention, voice output is used to verbalize responses to a user selecting an individual macro, such as from a macro library for recording. As the set of candidate macros may be very large, it is contemplated that the selection process will include an interaction between the reporting system and the user. Using a speech recognition user input device, the user refers to a macro by name or by using terminology familiar to the user that the user views as synonymous with the macro's name or contents. The reporting system then matches the user's utterance against the macro library to obtain a plurality of matching macros. If more than one matching macro is found, the system may respond by verbalizing the name and/or content of each matching macro and further requests—that is, prompts—the user to make a selection. Speech synthesized voice output enhances selection of a macro from a macro library whether the selection is done by navigating through a well-defined macro library categorization scheme or through the use of a more heuristic macro matching algorithm.

Each macro in a macro library has a name and a set of associated aliases, where an alias is a word or phrase used in clinical practice or a code from a clinical vocabulary that is synonymous to the macro's name or contents. Examples of clinical vocabularies include International Statistical Classification of Diseases and Related Health Problems version 9 (ICD-9), Logical Observation Identifiers Names and Codes (LOINC), Systematized Nomenclature of Human and Veterinary Medicine (SNOMED), Unified Medical Language System (UMLS), RadLex (a radiology lexicon), and other proprietary or user-specific medical vocabularies. It is contemplated that an alias may be assigned manually by the person creating a macro or automatically by the reporting system based on analysis of the macro's name or contents using techniques drawn from natural language processing, pattern matching, or medical coding—including analyses that may make use of clinical vocabularies and medical vocabulary tools such as the Unified Medical Language System (UMLS) Metathesaurus.

Matching a user's utterance with a macro can be done by comparing the words in the user's utterance with the words in each macro's name and aliases using text string pattern matching techniques. A more powerful heuristic approach to matching begins by processing the words in the user's utterance using natural language processing techniques such as stemming and keyword identification, optionally followed by the application of medical coding techniques, and including the use of clinical vocabularies and medical vocabulary tools. The resulting words or codes are then compared with each macro's name and aliases. Heuristic matching can adapt to user terminology preferences by analyzing historical patterns in the terminology that a user, or plurality of users, has spoken to invoke various macros and by basing future matches, in part, on the resulting associations.

In the macro library navigational approach, the macro library is represented as a structured categorization scheme—typically, a hierarchical tree structure consisting of macros and categories, or sub-hierarchies. The user speaks the name of a specific macro or category into a speech recognition mechanism. If the spoken macro name matches a macro in the macro library, then the reporting system performs the task of recording the macro and verbalizes an acknowledgement. If the spoken macro name is the name of a category, then the reporting system uses speech synthesis to verbalize the names and/or contents of the macros and/or subcategories contained within the specified category and further responds by prompting the user for a further, or refined, selection.

In embodiments implementing a heuristic macro selection algorithm, the user does not need to precisely speak the name of a macro or category. Instead, the user can use familiar clinical terminology. A heuristic algorithm incorporating natural language processing, pattern matching, and medical coding techniques identifies a plurality of macros that statistically match the spoken words of the user. If the result is a single macro, then the reporting system performs the task of recording that macro—after verbally requesting for confirmation in the case of an inexact match that falls below the statistical threshold for certainty. If the result is a plurality of macros, then the reporting system responds with the names, contents, or categories of the matching macros. With this heuristic approach, both the user and the system can be trained to adapt to each other—the user can gradually learn to use terms that yield the macros he or she needs to prepare the report and the reporting system can be trained to recognize macros (or categories) using alternative terms such as aliases.

As another example, speech synthesized voice output assists a user in preparing a report when a user requires a specific section or statement in the report. The user enters spoken words using a speech recognition user input device. The system responds with a section or statement in the report that corresponds to the words spoken by the user. If more than one section or statement matches the spoken words of the user, the system responds with speech synthesized voice output of the name or contents of each matching section or each matching statement. The system then prompts the user to make an additional, or refined, selection. The user may further speak information to the system using a speech recognition user input device to instruct the system to perform a specific task with the selected section or statement, for example, reading the section or statement aloud, or editing the section or statement such as adding a user spoken section or statement to the report, or replacing the section or statement with the user spoken information. Prior to performing the task on the selected section or statement, the system may confirm the task with the user, although it is contemplated the system can be configured to perform tasks without confirmation.

The user does not need to precisely speak the section or statement of the report. Instead, the user may speak words using familiar clinical terminology. The reporting system may use a heuristic matching algorithm incorporating natural language processing, pattern matching, and medical coding techniques to identify a plurality of sections or statements that statistically match the user spoken information. With this heuristic approach, both the user and the system can be trained to adapt to each other. In particular, the reporting system can be trained to recognize sections and statements using alternative terms.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

FIG. 1 illustrates the development of a CT angiography report by the use of system macros;

FIG. 4 illustrates the content of a radiology report, including organized sections, prepared by an embodiment of the reporting system according to the present invention;

DETAILED DESCRIPTION OF EMBODIMENTS OF THE INVENTION

The present invention is a reporting system that verbalizes information and by which certain types of users, such as medical professionals, can create a report 21 in an efficient manner while maintaining visual focus on the subject of the report or another subject or object. The present invention transmits a response as synthesized speech in response to information entered as user input via a user input device.

Figure 2:
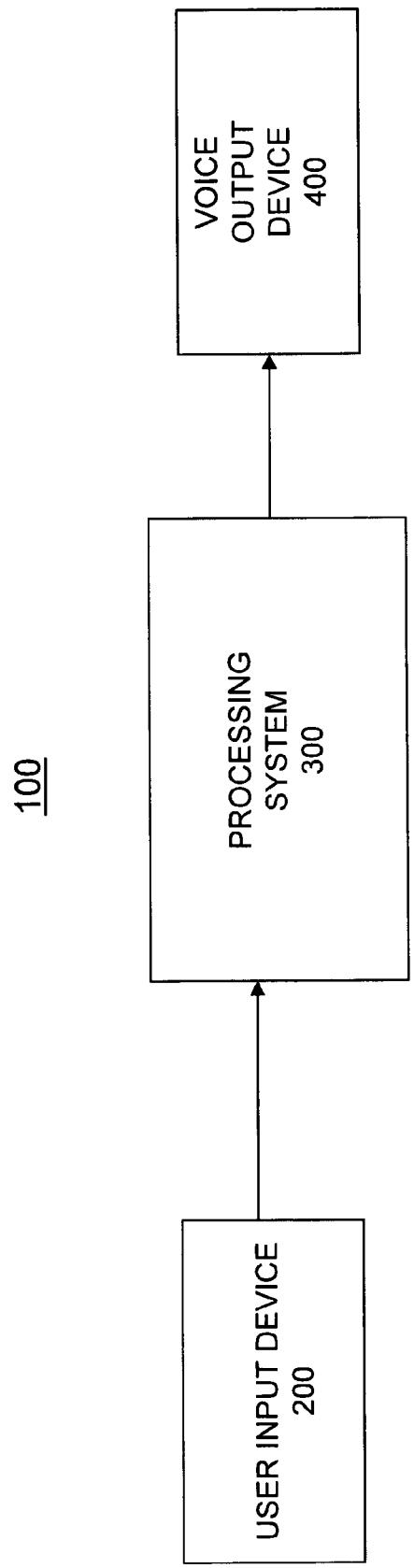
FIG. 2 illustrates an embodiment of a reporting system diagram according to the present invention.

FIG. 2 illustrates in diagram form an embodiment of a reporting system according to the present invention The reporting system 100 includes a user input device 200, a processing system 300 and a voice output device 400. Information is entered to the system 100 shown in FIG. 2, as user input via a user input device 200, such as keyboard, mouse, touch screen, keypad, and speech recognition mechanism.

The processing system 300 receives and processes the user input to perform a task. A response based on the task performed is prepared and communicated as voice output on a voice output device 400. The system can process the information including by accessing a heuristic algorithm, or accessing a database to correlate the information received to the task that the system is being directed to perform.

Figure 3:
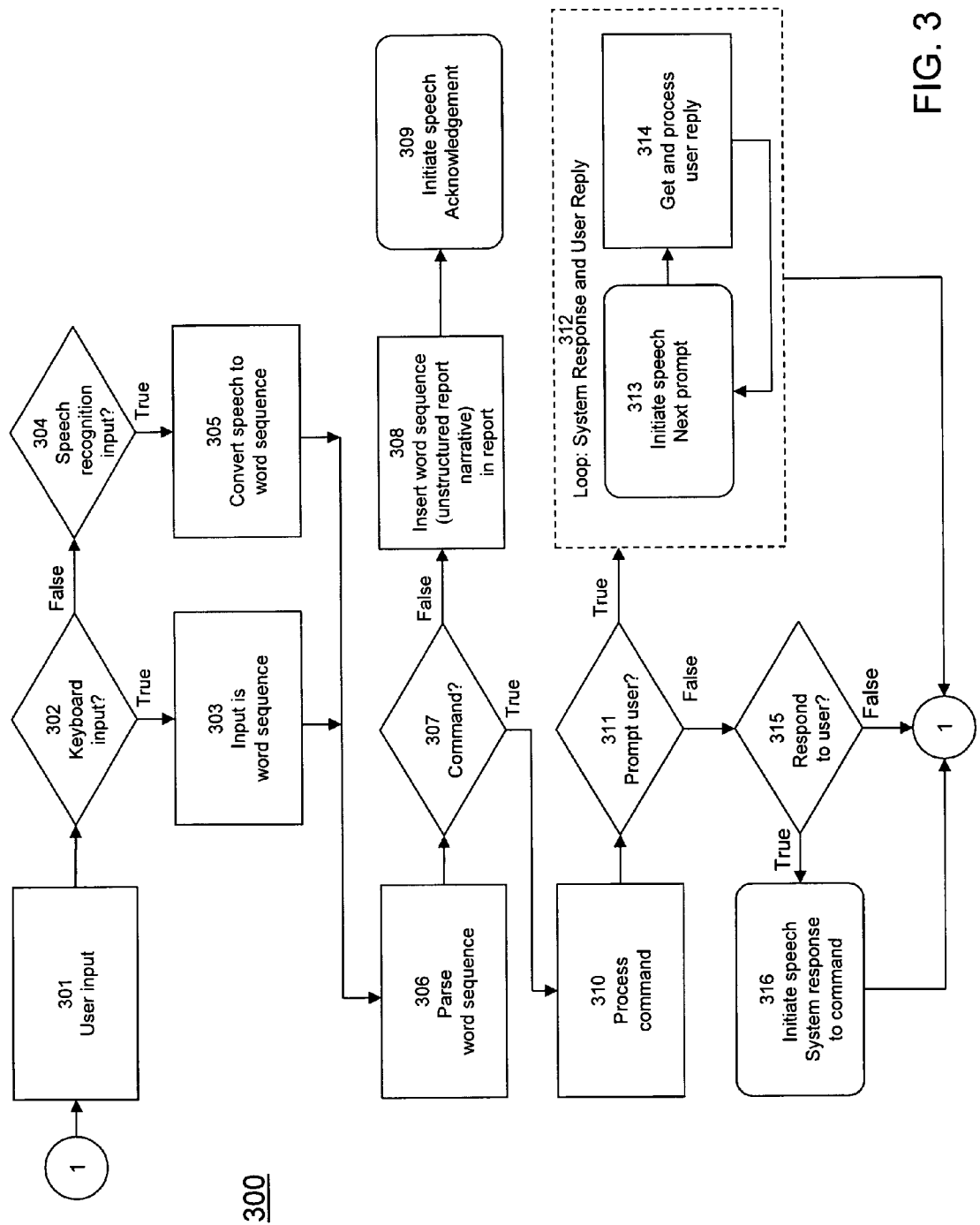
FIG. 3 is a flowchart of an embodiment of the reporting system according to the present invention.

FIG. 3 is a flowchart of an embodiment of the reporting system according to the present invention and, in particular, showing the operation of the processing system 300. Initially the report format, such as CT report, cardiology report, radiology report, is specified. The processing system 300 receives information as user input at step 301. If the input device 200 was a keyboard at step 302, then the system 300 may receive the input via engagement of one or more keys on the keyboard by the user. The input may include a sequence of typed words at step 303. The user may input information into the system 300 through a speech recognition mechanism. If the input device 200 is a speech recognition mechanism at step 304, then the user input can be a spoken word or words, or audio input, which is then converted to a sequence of words or input word sequence at step 305.

The illustrated processing system 300 then parses the input word sequence at step 306 and determines if it is an unstructured statement or a structured statement, such as a command at step 307. If the input word sequence is an unstructured statement, it is inserted into the report at step 308 and the system responds with a spoken acknowledgement at step 309. If the input word sequence is a command at step 307, or structured statement, then the processing system 300 processes the command including parameters at step 310 by correlating the command to the task the system is to perform. Depending on the task the system is directed to perform, the system may respond by prompting the user at step 311. Step 312 may include a plurality of responses such as prompts at step 313 to which the user enters additional information at step 314, such as entering data items or providing an additional, or refined, selection to the plurality of responses. The system 300 processes the additional information in the same manner as the initial input at step 301. If the system does not prompt the user at step 311, the system determines a response at step 315 and communicates the response as voice output at step 316.

FIG. 4 illustrates the content of one of the many types of reports 21 that can be prepared through use of the system 100, a radiology report 500 that has been organized into sections. The radiology report 500 includes the sections: clinical history 502; procedure 503; findings 504 (grouped into (sub) sections by anatomy, pathology or subprocedure); comparisons 506; and impressions 507. In one embodiment of the present invention, a user, such as a medical professional, enters information such as "Read report" to indicate that the reporting system 100 should read aloud the entire report or the medical professional enters information such as the command "Read section Lungs" to indicate that the reporting system 100 should read aloud a portion of the report, i.e., the "Lungs" section of the report.

As another example, the system according to the present invention permits a medical professional to speak information, such as the command "Summarize report", using a speech recognition user input device. The reporting system processes the information to perform the task of reading aloud a brief summary of the report contents such as names of the macros the medical professional used while creating the medical report, the contents of edited sections of the report that were recorded as macros and subsequently edited by the medical professional, and the contents of free text sections of the report, which are sections the medical professional added using unstructured statements on a speech recognition user input device or manually typed on a keyboard.

For example, a CT angiography report may contain the sections shown in FIG. 4 along with sections for the coronary arteries added within the findings section: left main artery (LM), left anterior descending artery (LAD), left circumflex artery (LCx), and right coronary artery (RCA). If a CT angiography report were created using the macro "Normal CTA", then a summary for this report may consist of the macro name alone being verbalized.

"Normal CTA"

If the user were to edit the statements recorded by the macro for the LAD and RCA sections of the report and add a recommendation to the "Impressions" section of the report, then the command "Summarize report" may result in the following synthesized speech:

"Normal CTA, except for the following sections:
LAD: [Statements in the LAD section of the report]
RCA: [Statements in the RCA section of the report]
Impressions: [Statements in the Impressions section of the report]"

Other examples include a medical professional accessing information from a patient's medical record. Since the volume of data relevant to a single patient can be very large and the portion related to the preparation of a particular medical report relatively small and since the relevancy of the data to a particular patient may change during preparation of the report, the present invention allows users to review selected or summarized content from a patient's medical record by providing information from user input via a user input device, such as by keyboard or by speaking into a microphone, "Read interpretations from last head CT" to transmit voice output of the "Interpretations" section from the report of the patient's last head CT scan; "Read last head CT, Section Cerebrum" to transmit voice output of detailed findings or interpretations related to a specific anatomical region—the cerebrum—in this same report; "Read last head CT, Section Lesions" to transmit voice output of detailed findings or interpretations related to a specific disease or pathology, in this case brain lesions; "Read last CBC" or "Read all liver function labs" to transmit voice output of specified lab data; "Read patient diagnoses" or "Read symptoms from last clinical encounter" to transmit voice output of information abstracted from clinical notes or the patient's EMR; "Read study order", or "Read patient data sheet" to transmit voice output of patient medical information from pre-study admissions paperwork; or "Read impressions from recent head CTs" to transmit voice output of the "Impressions" section from the plurality of reports for the patient's recent plurality of head CT scans.

The reporting system according to the present invention may use speech synthesis to indicate that a report input was recognized, for example by communicating the command that was invoked or the macro was recorded.

For example, suppose that a medical professional specifies that a macro should be recorded by speaking "Record macro Normal CTA". The system responds with a speech synthesized acknowledgement, such as the response "Macro Normal CTA recorded" in order to convey that the command was recognized by the system or that the macro was recorded.

The following are examples of system-communicated responses where the macro and report section names are not predefined. Thus, these responses cannot be communicated using pre-recorded speech, and must be generated using synthesized speech.

| User input information | System speech synthesized response |
|---|---|
| Macro Normal CTA | Normal CTA recorded, including sections LAD, RCA, . . . |
| Undo last macro | Macro CTA removed |
| Delete section LAD | Section LAD deleted |
| Edit section RCA | Section RCA selected for editing |

In addition to presenting the direct consequences of a command, speech synthesis can be used to communicate secondary consequences. For example, having recorded the macro "Normal CTA", a medical professional might record the macro "LAD occluded", which is designed to automatically replace the LAD section recorded by "Normal CTA" with a new LAD section that indicates that the LAD is occluded (blocked). Speech synthesis can be used to indicate that this replacement is being made—as shown in the following sequence of report inputs.

| User input information | System speech synthesized response |
|---|---|
| Macro Normal CTA | Normal CTA recorded, including sections LAD, RCA, . . . |
| Macro LAD occluded | LAD occluded recorded Section LAD replaced |

Speech synthesis can also immediately respond to user input on an input device, such as from a keyboard, mouse, or microphone, including that the user input is not recognized or that the system recognized command cannot be processed.

| User input information | System speech synthesized response |
|---|---|
| Macro Normal CTA | Macro Normal CTA does not exist |
| Delete section LAD | Section LAD does not exist |

The system of the present invention can prompt a medical professional with options resultant from a user input, such as a command. For example, in the case of a medical professional recording a macro, the system can use speech synthesis to ask the medical professional questions, such as whether the medical professional would like the macro summarized, "Macro X recorded. Summarize?". The medical professional can enter information, such as "Yes" or "Summarize macro" or "Read macro" such that the system responds by speaking the macro verbatim or in abbreviated (summarized) form.

Other examples include the system notifying the user when the current command results in content that conflicts with content already included in the report. For example, when recording a macro that includes data in a Section Y, the system may respond "Section Y already exists. Replace or append?" to prompt the user to indicate whether the existing content in Section Y should be replaced by the newly-recorded content (user responds with "Replace" as user input) or whether the newly-recorded content should be appended to the end of Section Y (user responds with "Append" as user input). As another example, the system can respond "Section Y differs from a prior report. Read conflicting statements?" to indicate that the current command results in data that conflicts with related or conflicting data existing in a prior report or elsewhere in the patient record.

In addition to prompting options resultant from the information entered by a user input, speech synthesis can be used to present responses from an analysis of the report as a whole. For example, when the medical professional indicates that a report is complete, the reporting system can check whether any required content is missing from the report and present spoken prompts for the missing content, as shown in the following example.

| User: | Sign report |
|---|---|
| System: | Report is missing the following required sections: |
| | Left ventricular function |
| | Calcium score |

The medical professional can then supply the missing content en masse. Alternatively, the reporting system can require that the user enter the missing content when so prompted as in the following example.

| User: | Sign report |
|---|---|
| System: | Report is missing the following required sections: |
| | Enter left ventricular function |
| | [Wait for and process user information] |
| | Enter calcium score |
| | [Wait for and process user information] |
| System: | Required content complete |
| | Sign report? |
| User: | Yes |
| System: | Report signed |

The system of the present invention can prompt a medical professional with options resultant from the user input information, such as a macro template. When a medical professional records a macro template, speech synthesis can be used to prompt the user to enter data in the expected fields. For example, recording the following macro template:
    There is a [STENOSIS] lesion in the [LOCATION]
may produce the speech synthesized prompt
    Coronary lesion recorded
    Please specify stenosis and location
If the user reply is

| Stenosis: | 50-70 percent |
|---|---|
| Location: | Mid LAD distal to D1 | the reporting system will place the following statement in the LAD section of the report:
    There is a 50-70 percent lesion in the mid LAD distal to D1.
It is also contemplated that the system can be more conversational such as having separate prompts for stenosis and location.

| User: | Macro coronary lesion |
|---|---|
| System: | Coronary lesion recorded |
| | Enter stenosis |
| User: | 50-70 percent |
| System: | Enter location |
| User: | Mid LAD distal to D1 | resulting in the statement:
    There is a 50-70 percent lesion in the mid LAD distal to D1.
This conversational reporting style can be readily extended to include a mix of required and optional fields, as illustrated in the following macro template:

There is a <STENOSIS> lesion in the [LOCATION]<IMPRESSION>
where the fields enclosed in angle brackets ("< >") are optional and can be left blank (omitted) using a "Next" command, as shown below:

| User: | Macro severe coronary lesion |
|---|---|
| System: | Severe coronary lesion recorded |
| | Enter location |
| User: | Mid LAD |
| System: | Enter optional stenosis |
| User: | Severe (>70%) |
| System: | Enter optional impression |
| User: | Next | resulting in the statement:
    There is a severe (>70%) lesion in the mid LAD.
    Further, the conversational dialogue can be extended to include pick-lists, as shown in the following macro template, where the pick-list options are of the form (selection identifier: text). Note that in this example "stenosis" is a required field with a pick-list of choices denoted by ▼.
    There is a [STENOSIS ▼] lesion in the [LOCATION] <IMPRESSION>
    Mild: mild (<30%)
    Moderate: moderate (30-50%)
    Moderately-severe moderately severe (50-70%)
    Severe: severe (>70%)
The following dialogue:

| User: | Macro coronary lesion |
|---|---|
| System: | Coronary lesion recorded |
| | Select stenosis from mild, moderate, moderately-severe, severe |
| User: | Moderate |
| System: | Enter location |
| User: | Mid LAD |
| System: | Enter optional impressions |
| User: | The distal vessel is normal-sized, shows no disease, and supplies a moderately-sized vascular territory. The lesion is a likely culprit for the patient's anginal symptoms. | yields the statement:
    There is a moderate (30-50%) lesion in the mid LAD. The distal vessel is normal-sized, shows no disease, and supplies a moderately-sized vascular territory. The lesion is a likely culprit for the patient's anginal symptoms.
Alternatively, the prompt, such as the stenosis prompt, could omit the pick-list choices:

| User: | Macro coronary lesion |
|---|---|
| System: | Coronary lesion recorded |
| System: | Select stenosis |
| User: | Moderate | and allow the medical professional to ask for the list using a "List choices" command when needed:

| User: | Macro coronary lesion |
|---|---|
| System: | Coronary lesion recorded |
| System: | Select stenosis |
| User: | List choices |
| System: | Mild, moderate, moderately-severe, severe |
| User: | Moderate |

The conversational dialogue can further support macro templates which provide the framework for an entire report. A very simple report template is shown below, where the fields enclosed in angle brackets ("< >") are optional.

Procedure
        A standard thoracic CT was performed.
    Findings
        Lungs: <LUNGS>
        Heart: <HEART>
        Mediastinum: <MEDIASTINUM>
    Conclusions
        <CONCLUSIONS> with the following dialogue:

| | |
|---|---|
| User: | Macro Chest CT |
| System: | Chest CT recorded |
| | Enter lungs |
| User: | Lungs appear normal, with no masses or indications of disease. |
| System: | Enter heart |
| User: | Heart appears slightly enlarged. No evidence of endocardial disease. |
| System: | Enter mediastinum |
| User: | Next |
| System: | Enter conclusions |
| User: | Normal chest CT. No indication of old or new pneumonia or of inflammation of the pleura. | yielding the report:
    Exam type
        A standard thoracic CT was performed.
    Findings
        Lungs: Lungs appear normal, with no masses or indications of disease.
        Heart: Heart appears slightly enlarged. No evidence of endocardial disease.
    Conclusions
        Normal chest CT. No indication of old or new pneumonia or of inflammation of the pleura.

Again, information can be spoken using a speech recognition user input device or entered via a keyboard or mouse. For example, the "Next" command in the example above could be entered by clicking the "▶"(forward arrow) button on a dictation device. Similarly, a user can command the system to return to a prior field by clicking the "◀"(backward arrow) button on the dictation device.

Figure 5:
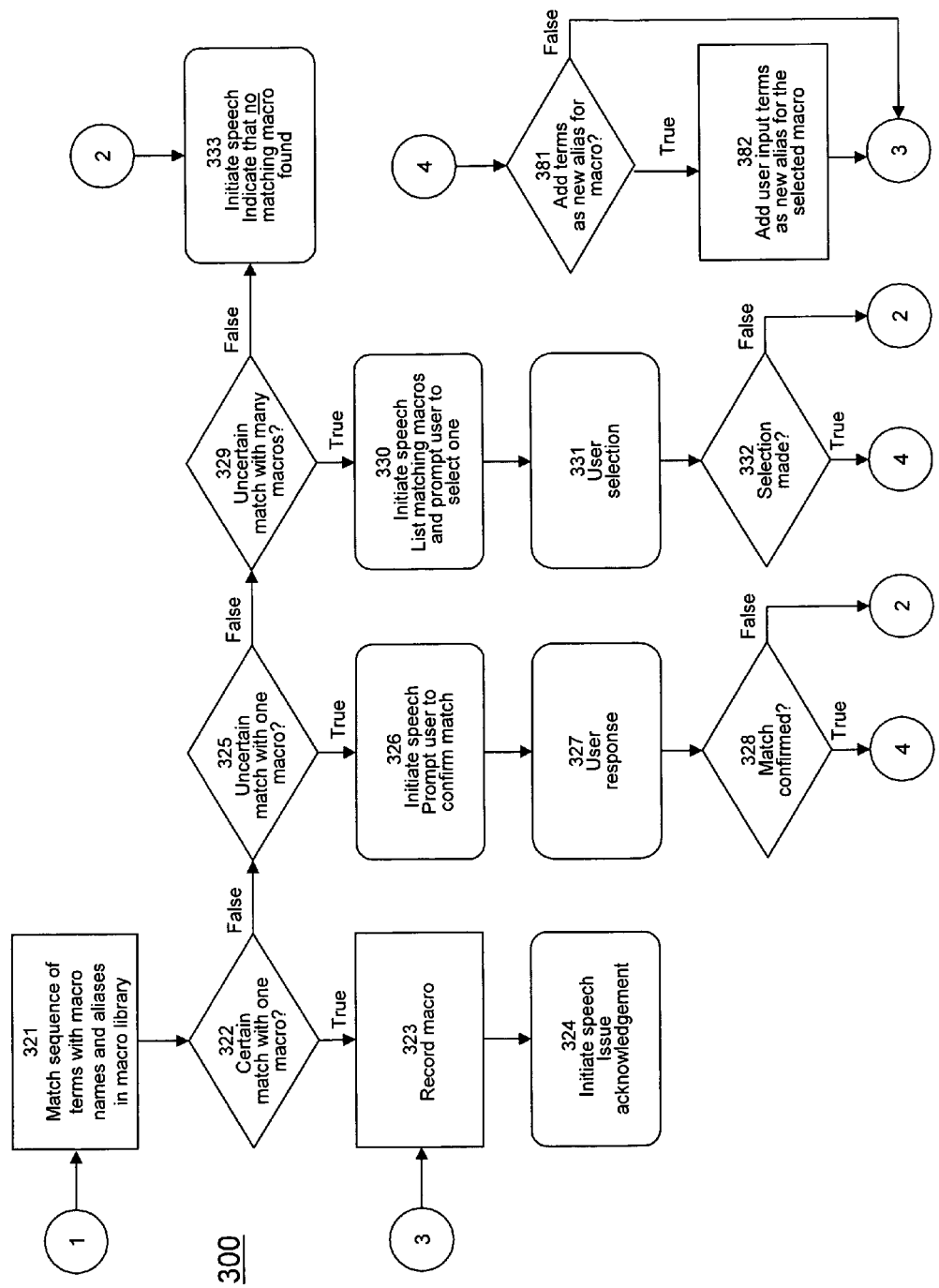
FIG. 5 is a flowchart of an embodiment of the reporting system for selecting macros according to the present invention.
Figure 6:
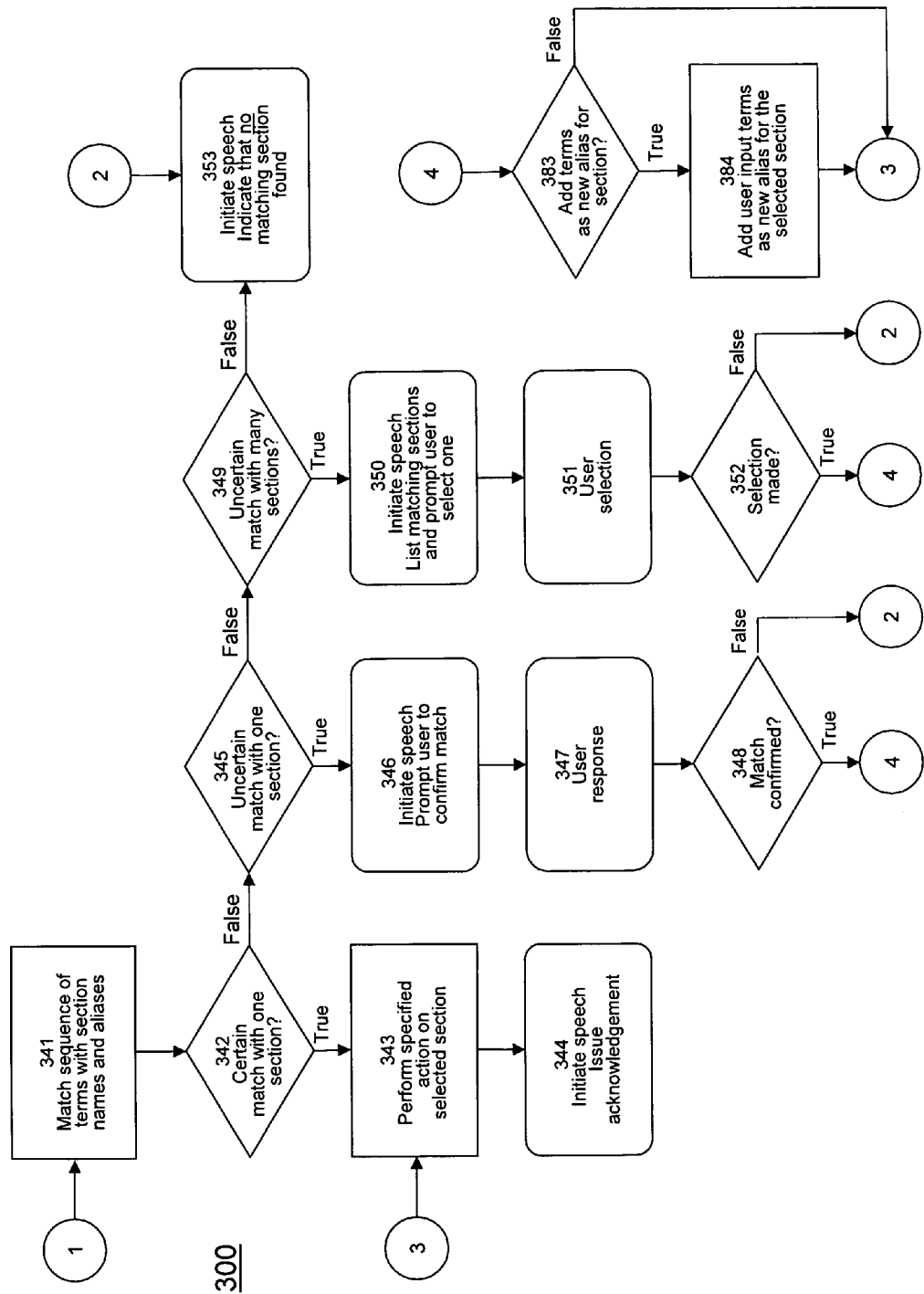
FIG. 6 is a flowchart of an embodiment of the reporting system for selecting sections in a report according to the present invention.

More particularly, FIGS. 5-6 are flowcharts illustrating various embodiments of the processing system 300 of the reporting system 100 for selecting macros, sections and statements of a report. FIG. 5 illustrates macro invocation wherein the information input by the user on a speech recognition mechanism is a word, words, or statement to perform the task of selecting a macro from a macro library. It is contemplated the information includes a macro name or an alias, which is terminology familiar to the user such as a word, words, statement, or code from a clinical vocabulary that is treated as synonymous with a macro's name or contents.

The processing system 300 processes the information and performs the task of matching the information with the name or alias of a macro in the macro library at step 321. Each macro in a macro library has a name and a set of associated aliases, where an alias is a word, words, statement, or code from a clinical vocabulary that is treated as synonymous to the macro's name or contents.

In one embodiment, matching the macro uses a heuristic algorithm. The heuristic algorithm uses natural language processing, pattern matching, and medical coding to identify a plurality of macro names and aliases that statistically match the information input by the user. It is contemplated that matching the macro may be based on a word, words, or statement itself or on an underlying coded representation of the information derived from clinical vocabulary or other vocabulary tools. It is further contemplated that heuristic matching may adapt to user terminology preferences by analyzing historical patterns in the terminology that a user, or plurality of users, has spoken to invoke various macros and by basing future matches, in part, on the resulting associations.

Figure 5A:
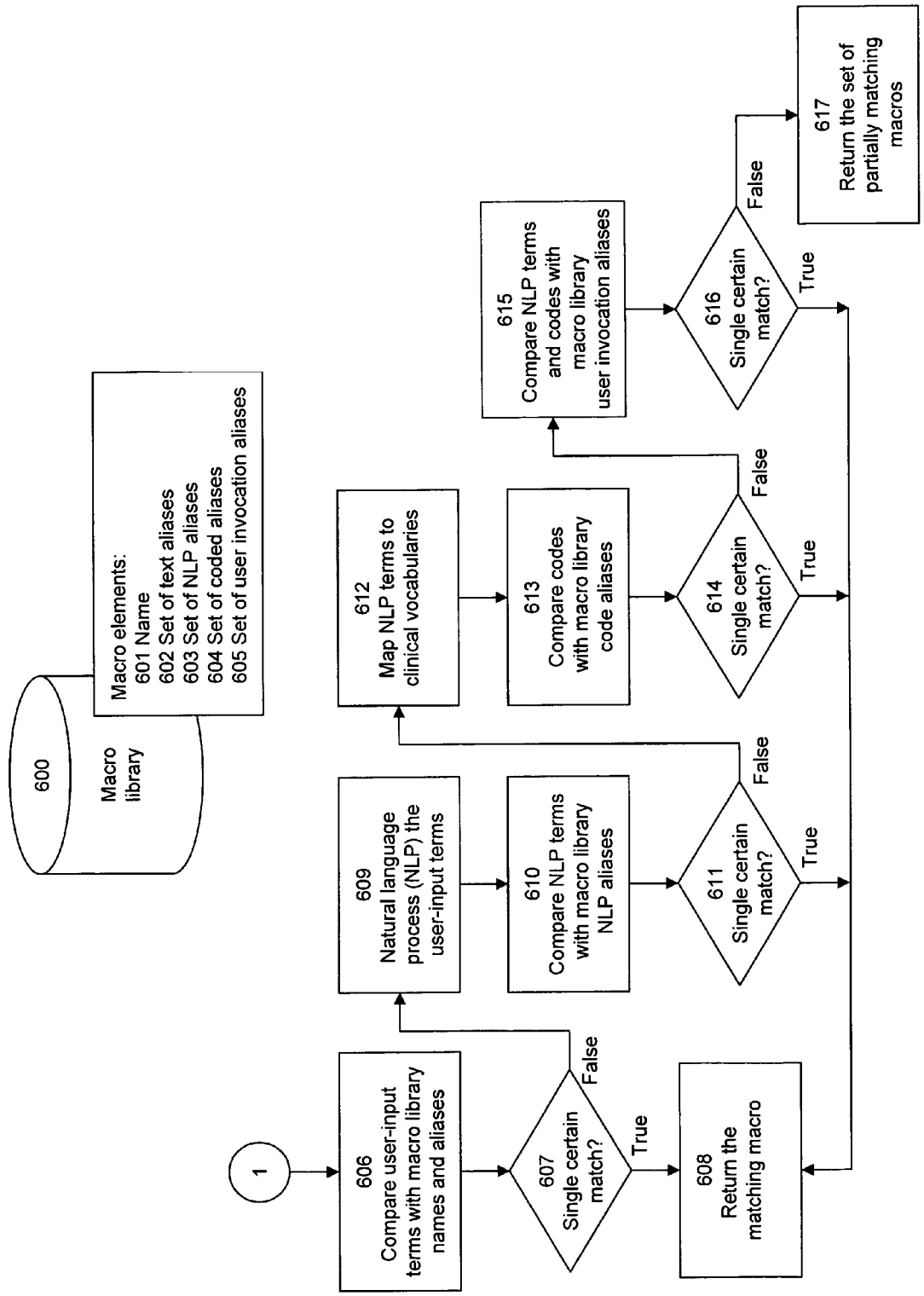
FIG. 5a is a flowchart of an embodiment of a heuristic algorithm for selecting macros from a macro library according to the present invention.

FIG. 5a is a flowchart of an embodiment of a heuristic algorithm for selecting macros from a macro library according to the present invention. Each macro in the macro library 600 has each of the following associated elements: name 601; set of text aliases 602; set of natural language processed (NLP) aliases 603; set of coded aliases 604; and a set of user invocation aliases 605.

NLP aliases 603 are derived from a macro name 601 and text aliases 602 through the application of natural language processing techniques such as filtering out unimportant words and reducing the remaining words to their stem or root form.

Coded aliases 604 are derived from the NLP text aliases 603 by mapping each alias to terms in a coded clinical vocabulary, thereby producing a set of codes for each macro.

User invocation aliases 605 are derived from the set of words or statements that a user, or plurality of users, has spoken when invoking a macro in the past or the codes associated with these words or statements. The aliases are produced using the same NLP techniques used in creating the NLP aliases 603, as well as the same code mapping techniques used in creating the coded aliases 604.

The set of NLP aliases 603, set of coded aliases 604, and set of user invocation aliases 605 are derived when the macro library is created or updated.

After the information is received from the user input via the user input device, the information is matched with the name or alias of a macro in the macro library by using a heuristic algorithm. In this embodiment, the information received is a term or terms, such as a word, words, or statement. In step 606, the terms are compared with the names 601 and text aliases 602 from the macro library 600. If an exact match or a partial match exceeding a statistical threshold for certainty is found at step 607, then the matching macro is returned at step 608.

If an exact match or a partial match exceeding a statistical threshold for certainty is not found in step 607, then the terms received from the user input are processed in step 609 using NLP techniques. The NLP processed terms are then compared with the NLP aliases 603 of the macro library 600 at step 610. If an exact match or a partial match exceeding a statistical threshold for certainty is found at step 611, then the matching macro is returned at step 608.

If no certain matches are found at step 611, then the NLP processed terms produced at step 609 are mapped to a coded clinical vocabulary at step 612. The mapped codes are then compared to the coded aliases 604 from the macro library 600 at step 613. If an exact match or a partial match exceeding a statistical threshold for certainty is found at step 614, then the matching macro is returned at step 608.

If no certain matches are found at step 614, then the NLP processed terms produced at step 609 and the mapped codes at step 612 are compared with the user invocation aliases 605 from the macro library 600 at step 615. If an exact match or a partial match exceeding a statistical threshold for certainty is found at step 616, then the matching macro is returned t step 608. If none of the previous steps produce a certain match, then a set of partially matching macros produced in step 606, step 610, step 613, and step 615 are returned at step 617.

The steps of the heuristic algorithm described above can occur in any contemplated order. In addition, certain steps can be removed from the heuristic algorithm and steps for selecting macros from a macro library known to those skilled in the art can be added to the heuristic algorithm.

Returning to FIG. 5, if the resulting match is a single macro and the statistical certainty of the match is above a statistical threshold for certainty at step 322, then the system performs the task of recording the macro at step 323 and the system 300 verbalizes an acknowledgement, such as the macro name "Macro X recorded", at step 324 using speech synthesis.

If the resulting match is a single macro, but the statistical certainty of the match falls below a statistical threshold for certainty at step 325, then the processing system 300 responds using speech synthesis with a prompt to the user at step 326. The user enters additional information at step 327, either verbally using speech recognition, by clicking a button via a user input device such as a microphone, by clicking a on-screen button with a mouse or touching it using a touch screen, or by pressing a key on a keyboard. If the user enters information that confirms the match at step 328, then the macro is recorded at step 323 and the system verbalizes an acknowledgement at step 324. If the user enters information that does not confirm the match at step 328, the processing system 300 responds at step 333 that no matching macro was found.

If the resulting match is a plurality of macros, but the statistical certainty of the match falls below a statistical threshold for certainty at step 329, then the processing system 300 responds using speech synthesis at step 330. The response at step 330 includes the names or contents of the matching macros. The user then selects a macro from this plurality at step 331 via a user input device as described above. If the user selects a macro at step 332, then the macro is recorded at step 323 and the system verbalizes an acknowledgement at step 324. If the user does not select a macro at step 332, the processing system 300 responds at step 333 that no matching macro was selected.

This selection process can be extended to support hierarchical macro libraries that group related macros into categories by extending the matching process to include the names and aliases of categories, as well as those of individual macros.

After selection of a macro in step 328 or step 332, the processing system 300 may verbalize a response at step 381 asking whether the information of the utterance of the user should be added as a new alias for the macro the user selected in step 328 or step 332. If the user replies affirmatively, the alias is added at step 382 and the macro is recorded at step 323. If the user replies negatively, the alias is not added and the macro is recorded at step 323.

Another embodiment of the invention uses speech synthesis to assist a medical professional in preparing a medical report by identifying the section in a report that corresponds to a word, words, or statement spoken by the medical professional as shown in FIG. 6, where the spoken information includes a section name or terminology familiar to the user that the user views as synonymous with a section's name or potential contents. It is contemplated that each section has a section name and a set of associated aliases, where an alias is terminology familiar to the user such as a word, words, statement, or code from a clinical vocabulary that is treated as synonymous to the section's name or potential contents.

The processing system 300 processes the information and performs the task of matching the information with the name or alias of a section of the report at step 341. In one embodiment, matching the section uses a heuristic algorithm. The heuristic algorithm uses natural language processing, pattern matching, and medical coding to identify a plurality of section names and aliases that statistically match the information input by the user. It is contemplated that matching the section may be based on a word, words, or statement itself or on an underlying coded representation of the information derived from clinical vocabulary or other vocabulary tools. It is further contemplated that heuristic matching may adapt to user terminology preferences by analyzing historical patterns in the terminology that a user, or a plurality of users, has spoken to invoke various sections and by basing future matches, in part, on the resulting associations.

If the resulting match is a single section and the statistical certainty of the match is above a statistical threshold for certainty at step 342, then the system performs a task at step 343 and the system 300 verbalizes an acknowledgement, such as such as "Section X replaced", at step 344 using speech synthesized voice output. The task performed on the selected section at step 343 may be specified explicitly by the user such as "Read section X" or "Delete section X". The specified task may further be implicit such as adding the spoken phrase or statement to the selected section. Examples of tasks specified by the user include: reading the section aloud, adding the spoken statement to the section, or replacing the contents of the section, such as narrative statements in the section, with the spoken statement. Prior to executing the specified task on a section within the report, the system can confirm the task with the user, although it is contemplated the system can be configured perform such tasks without confirmation.

If the resulting match is a single section but the statistical certainty of the match falls below a statistical threshold for certainty at step 345, then the processing system 300 responds using speech synthesis with a request for the user to confirm the match at step 346. The user enters additional information at step 347, either verbally using speech recognition, by clicking a button via a user input device such as a microphone, by clicking a on-screen button with a mouse or touching it using a touch screen, or by pressing a key on a keyboard. If the user enters information that confirms the match at step 348, the processing system 300 performs the specified task at step 343 and verbalizes an acknowledgement at step 344. If the match is not confirmed at step 348, then the system responds with a verbalized warning at step 353 that no matching section was found.

If the resulting match is a plurality of sections, but the statistical certainty of the match falls below a statistical threshold for certainty at step 349, then the processing system 300 responds using speech synthesis at step 350. The response at step 350 includes the names or contents of the matching sections. The user then selects a section from this plurality at step 351 using a user input device. If the user selects a section at step 352, the processing system 300 performs the specified task at step 343 and verbalizes an acknowledgement at step 344. If a section is not selected at step 352, the processing system 300 responds at step 353 with a warning that no matching section was found.

After selection of a section in step 348 or step 352, the processing system 300 may verbalize a response at step 383 asking whether the information of the utterance of the user should be added as a new alias for the section the user selected in step 348 or step 352. If the user replies affirmatively, the section is added at step 384 and the specified task is performed at step 343. If the user replies negatively, the alias is not added and specified task is performed at step 343.

Figure 7:
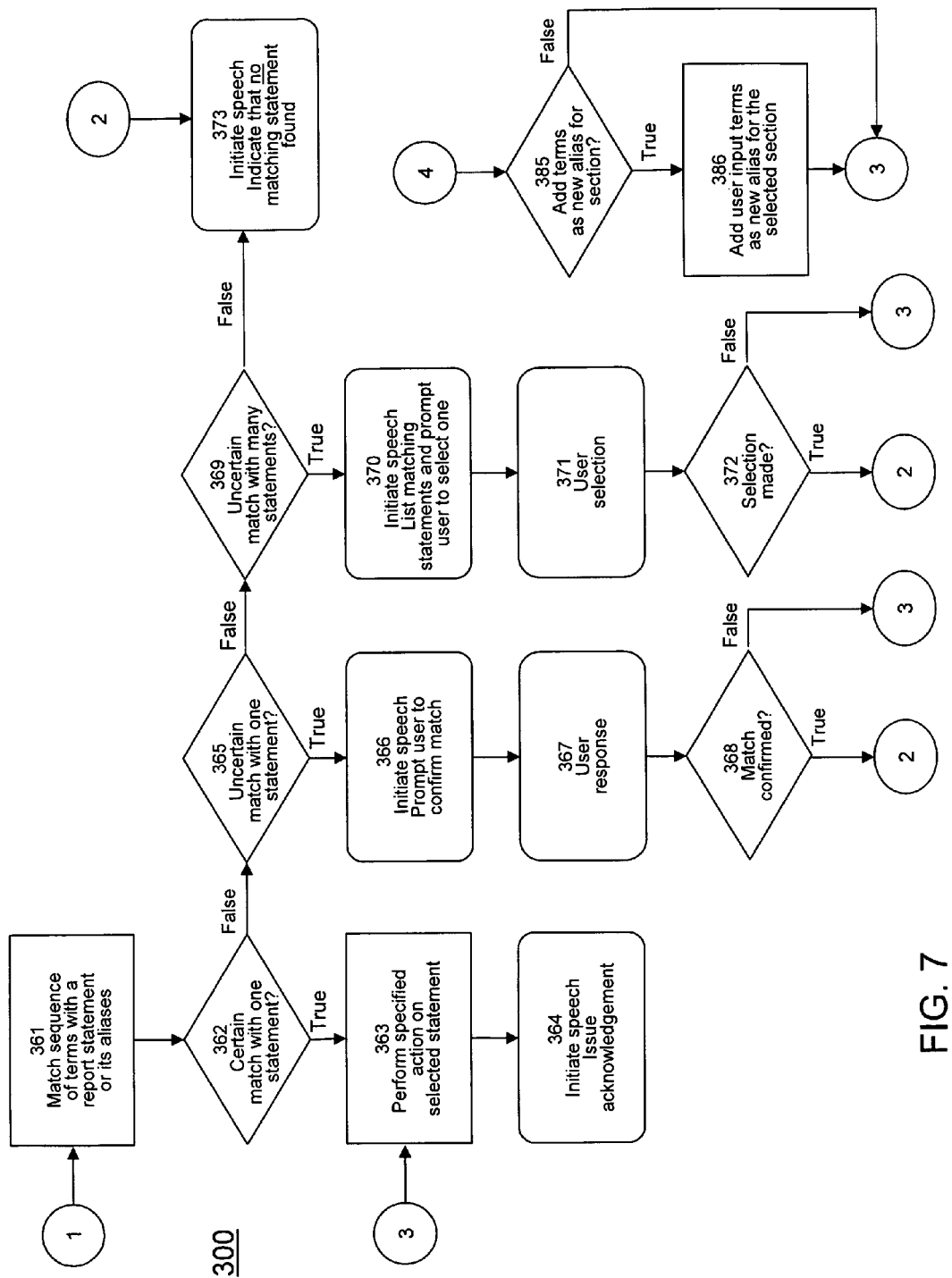
FIG. 7 is a flowchart of an embodiment of the reporting system for selecting statements in a report according to the present invention.

As shown in FIG. 7, another embodiment of the invention uses speech synthesis to assist a medical professional in identifying the statement (or statements) in a report that match a statement spoken by the medical professional. It is contemplated each statement may include a set of associated aliases from a clinical vocabulary. The set of associated aliases is synonymous with the content of the statement.

The processing system 300 processes the information and performs the task of matching the information with the contents or alias of a statement or statements of the report at step 361. In one embodiment, matching the statement uses a heuristic algorithm. The heuristic algorithm uses natural language processing, pattern matching, and medical coding to identify a plurality of statements that statistically match the information input by the user. It is contemplated that matching the statement may be based on a word, words, or statement itself or on an underlying coded representation of the information derived from clinical vocabulary or other vocabulary tools.

If the resulting match is a single statement and the statistical certainty of the match is above a statistical threshold for certainty at step 362, then the system performs a task at step 363 and the system 300 verbalizes an acknowledgement at step 364 using speech synthesized voice output. The task performed on the selected statement at step 363 may be explicit or implicit such as noting that a statement exists with the acknowledgement "Conflicting statement found", reading the selected statement aloud, marking the selected statement for subsequent editing or deletion, or replacing the selected statement with the spoken statement. Prior to executing the specified task on a statement within the report, the system can confirm the task with the user, although it is contemplated the system can be configured perform such tasks without confirmation.

If the resulting match is a single statement but the statistical certainty of the match falls below a statistical threshold for certainty at step 365, then the processing system 300 responds using speech synthesis with a request for the user to confirm the match at step 366. The user enters additional information at step 367, either verbally using speech recognition or manually using an input device. If the user enters information that confirms the match at step 368, the processing system 300 performs the specified task at step 363 and verbalizes an acknowledgement at step 364. If the match is not confirmed at step 368, then the system responds with a verbalized warning at step 373 that no matching statement was found.

If the resulting match is a plurality of statements, but the statistical certainty of the match falls below a statistical threshold for certainty at step 369, speech synthesis verbalizes the matching statements at step 370. The user then selects one or more statements from this plurality at step 371 using a user input device. If the user selects a statement or statements at step 372, the processing system 300 performs the specified task at step 363 and verbalizes an acknowledgement at step 364. If a statement is not selected at step 372, the processing system 300 responds at step 373 with a warning that no matching statement was found.

After selection of a section in step 368 or step 372, the processing system 300 may verbalize a response at step 385 asking whether the information of the utterance of the user should be added as a new alias for the report statement the user selected in step 368 or step 372. If the user replies affirmatively, the section is added at step 386 and the specified task is performed at step 363. If the user replies negatively, the alias is not added and specified task is performed at step 363.

Report review can be conducted as a conversational dialogue allowing the medical professional to proofread and edit the report, for example, with a speech recognition input device. Following is an example of a medical professional invoking a complete review of the report:

| User: | Read report | |
|---|---|---|
| System: | Left ventricle: | [Statements in the LAD section] |
| | LAD: | [Statements in the LAD section] |
| | RCA: | [Statements in the RCA section] |
| | Impressions: | [Statements in the Impressions section] | or a summary of the report:

| User: | Summarize report | |
|---|---|---|
| System: | Normal CTA except for the following: | |
| | RCA: | [Statements in the RCA section] |
| | Impressions: | [Statements in the Impressions section] | or the review of a specific section of the report:

| User: | Read section Impressions | |
|---|---|---|
| System: | Impressions: | [Statements in the Impressions section] |

The following are exemplary commands that the medical professional can speak, even during the system response:

| Command | Task |
|---|---|
| Next | Skip current section, continue with next section. |
| Back | Continue with previous section. |
| Stop reading | Stop reading of the report |
| Resume reading | Resume reading of the report |
| Delete | Delete the current sentence |
| Edit | On-screen editing of the current sentence |
| Replace . . . statements . . . | Replace current sentence with spoken statements |
| Insert . . . statements . . . | Insert the spoken statements |
| Delete section X | Delete specified section |
| Edit section X | On-screen editing of the current section |
| Replace section X . . . statements . . . | Replace specified section with spoken statements |
| Insert section X . . . statements . . . | Insert specified section containing spoken statements |

These commands can also be interspersed with the recording of additional macros (e.g., "Macro X")—including those macros that replace portions of the report and macro templates.

The dialogue with respect to reviewing patient data allows a medical professional to specify the scope of the review. For example, the medical professional can enter information to have the data read aloud or indicate that the data should be skipped. A sample dialogue includes:

| User: | Read reports 'Head CT' |
|---|---|
| System: | Head CT, Jan. 4, 2007 |
| User: | Summary |
| System: | [Summary from the selected report] |
| System: | Head CT, Nov. 14, 2006 |
| User: | Section 'Cerebrum' |
| System: | [Contents of section 'Cerebrum' from the selected report] |

-continued

| System: | Head CT, Oct. 23, 2005 |
| User: | Section 'Cerebrum' |
| System: | No section 'Cerebrum' |
| User: | Skip |

A similar approach can be used in the review of the medical literature such as current medical abstracts, on-line textbooks and Web resources. The medical professional can specify, for example, the resources to search and what keywords to search. For example, as the literature is communicated as voice output, the medical professional can enter information to have details regarding that item be read aloud or indicate that the data should be skipped. A sample dialogue includes:

| User: | Search recent abstracts 'CT left ventricular function' |
| System: | RSNA 2006, "Comprehensive Global and Regional Left Ventricular Function and Myocardial Perfusion Analysis by 64-slice MDCT in Patients with Acute Myocardial Infarction" |
| User: | Abstract |
| System: | [Abstract from the selected paper] |
| User: | Print paper |
| System: | Paper printed |
| System: | International Journal of Biomedical Imaging, 2006, "Assessment of Left Ventricular Function in Cardiac MSCT Imaging by a 4D Hierarchical Surface-Volume Matching Process" |
| User: | Skip |
| System: | European Radiology, 2006, "Global left ventricular function in cardiac CT. Evaluation of an automated 3D region-growing segmentation algorithm" |
| User: | Abstract |
| System: | [Abstract from the selected paper] |

The examples above emphasize the use of speech synthesis in conjunction with a reporting system in which the medical professional leads the conversation, directing the reporting system via commands. Speech synthesis can also be used in conjunction with a reporting system in which the system guides the user through the reporting process.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A method for a user to create a report through voice output, comprising:
(a) receiving by a computer information from user input via a user input device;
(b) processing by the computer the information, wherein said processing step utilizes a heuristic algorithm;
(c) performing by the computer a task resultant from said processing step, wherein said performing step further comprises a step of making a heuristic selection of one or more macros from a macro library;
(d) preparing by the computer a response based on said performing step;
(e) communicating the response as voice output verbalized through use of a voice output device; and
(f) repeating said steps (a)-(e) until the report is completed.

2. The method of claim 1, wherein the user input device is a speech recognition mechanism.

3. The method of claim 1, wherein said performing step further comprises a step of selecting a section of the report.

4. The method of claim 1, wherein said performing step further comprises a step of selecting a statement of the report.

5. The method of claim 1, wherein the heuristic selection of the macro is based on matching the information received from the user input via the user input device with a macro name.

6. The method of claim 1, wherein the heuristic selection of the macro is based on matching the information received via the user input on the user input device with macro content.

7. The method of claim 3, wherein said selecting a section of the report step comprises a step of matching the information received from the user input via the user input device with a section of the report.

8. The method of claim 4, wherein said selecting a statement of the report step comprises a step of matching the information received from the user input via the user input device with a statement of the report.

9. The method of claim 5, wherein the information received from the user input via the user input device includes terminology that is synonymous with the macro name.

10. The method of claim 6, wherein the information received from the user input via the user input device includes terminology that is synonymous with the macro content.

11. The method of claim 8, wherein the information received from the user input via the user input device includes terminology that is synonymous with the statement content.

12. The method of claim 1, wherein said communicating step further comprises a step of saving the voice output as part of the report.

13. The method of claim 1, wherein said communicating step further comprises the step of listing partially matching macros.

14. The method of claim 13, wherein said listing partially matching macros step further comprises the step of selecting by the user a macro.

15. The method of claim 1, wherein said communicating step further comprises the step of listing matching categories.

16. The method of claim 1, wherein said processing step further comprises a step of using a coded representation of the user input derived from a clinical vocabulary.

17. The method of claim 1, wherein the heuristic selection of the macro is based on historical patterns of the information received via the user input on the user input device.

18. The method of claim 1, wherein the report is a medical report.

19. The method of claim 1, wherein the information received via the user input on the user input device is an unstructured statement.

20. The method of claim 1, wherein the information received via the user input on the user input device is a structured statement.

21. The method of claim 1, wherein said communicating step further comprises a step of saving the voice output as an audio file.

22. The method of claim 1 wherein said communicating step further comprises a step of confirming said processing step.

23. The method of claim 1, wherein said communicating step is activated automatically.

24. The method of claim 1, wherein said communicating step is activated verbally with a speech recognition mechanism.

25. The method of claim 1, wherein said communicating step further comprises a step of interrupting the response to initiate said receiving step.

26. The method of claim 1, wherein said performing step further comprises a step of annotating an image.

27. The method of claim 26, wherein the image is a diagram.

28. A system for a user to prepare a current report comprising:
- a user input device to enter information from a user input;
- a reporting system to receive and process the information by executing a heuristic algorithm,
- said reporting system structured to perform a task and prepare a response based on the performance of the task, wherein the task is a heuristic selection of one or more macros from a macro library; and
- a voice output device to communicate the response aurally as voice output.

29. The system of claim 28, wherein the voice output is synthesized speech.

30. The system of claim 28 further comprising a display device to illustrate the information.

31. The system of claim 28, wherein said user input device is a speech recognition mechanism.

32. The system of claim 28, wherein the response is a narrative of medical literature.

33. The system of claim 28, wherein the response is a prompt to enter additional information.

34. The system of claim 28, wherein the response is a list of choices from which the user can select a choice.

35. The system of claim 28, wherein the response is at least a portion of the current report.

36. The system of claim 28, wherein the response is a summary of the current report.

37. The system of claim 28, wherein the response is content from a prior report.

38. The system of claim 28, wherein the information entered on the user input specifies at least a portion of the response for transfer to the current report.

39. The system of claim 28, wherein the response is content from a medical record.

40. The system of claim 28, wherein the response is a conflict within the current report.

41. The system of claim 28, wherein the response is a conflict between the information and a medical record.

42. The system of claim 28, wherein the response is missing information from the current report.

43. The system of claim 28, wherein the response is an alert.

44. The system of claim 43, wherein the alert is transmitted by one of the following: telephone, voice mail, message bank, physician notification system, or Web page.

45. The system of claim 28, wherein the task is annotating a portion of the current report.

46. The system of claim 45, wherein the portion of the current report is an image.

47. The system of claim 46, wherein the image is a diagram.

* * * * *